United States Patent
Vogler et al.

(10) Patent No.: US 10,433,722 B2
(45) Date of Patent: Oct. 8, 2019

(54) DIAGNOSIS SYSTEM AND DIAGNOSIS METHOD

(71) Applicant: Wavelight GmbH, Erlangen (DE)

(72) Inventors: Klaus Vogler, Erlangen (DE); Christof Donitzky, Erlangen (DE)

(73) Assignee: WAVELIGHT GMBH, Erlangen ( * ) Notice: Subject to any disclaimer, the term of this patent is extended or adjusted under 35 U.S.C. 154(b) by 291 days.

(21) Appl. No.: 14/914,600

(22) PCT Filed: Oct. 11, 2013

(86) PCT No.: PCT/EP2013/071323
§ 371 (c)(1),
(2) Date: Feb. 25, 2016

(87) PCT Pub. No.: WO2015/051854
PCT Pub. Date: Apr. 16, 2015

(65) Prior Publication Data
US 2016/0206194 A1    Jul. 21, 2016

(51) Int. Cl.
*A61B 3/10*  (2006.01)
*A61B 3/14*  (2006.01)
(Continued)

(52) U.S. Cl.
CPC ............ *A61B 3/102* (2013.01); *A61B 3/0025* (2013.01); *A61B 3/107* (2013.01); *A61B 3/1025* (2013.01);
(Continued)

(58) Field of Classification Search
CPC ........... A61B 3/107; A61B 3/103; A61B 3/14; A61B 3/113; A61B 3/1225; A61B 3/024; A61B 3/032; A61B 3/18; A61B 3/1015
(Continued)

(56) References Cited

U.S. PATENT DOCUMENTS 5,795,295 A  *  8/1998  Hellmuth  ............. A61B 5/0059
                                                     250/201.3
7,777,891 B2    8/2010  Hasegawa
(Continued)

FOREIGN PATENT DOCUMENTS

DE    102005006724 A1    8/2006
JP    2013-208395        10/2013
(Continued)

OTHER PUBLICATIONS

Matthew R. Ford et al.; "Method for optical coherence elastography of the cornea"; Journal of Biomedical Optics; vol. 16; No. 1; Jan. 1, 2011; p. 016005; ISSN: 1083-3668.
(Continued)

*Primary Examiner* — Dawayne Pinkney

(57) ABSTRACT

A diagnosis system and a diagnosis method are provided. More specifically, embodiments of the present disclosure relate to a diagnosis system for detection of corneal degeneration impacting the biomechanical stability of the human cornea and a diagnosis method for detection of corneal degeneration impacting the biomechanical stability of the human cornea. Still more specifically, embodiments of the present disclosure relate to a diagnosis system for early detection of corneal degeneration impacting the biomechanical stability of the human cornea and a diagnosis method for early detection of corneal degeneration impacting the biomechanical stability of the human cornea.

7 Claims, 3 Drawing Sheets

Figure 1:
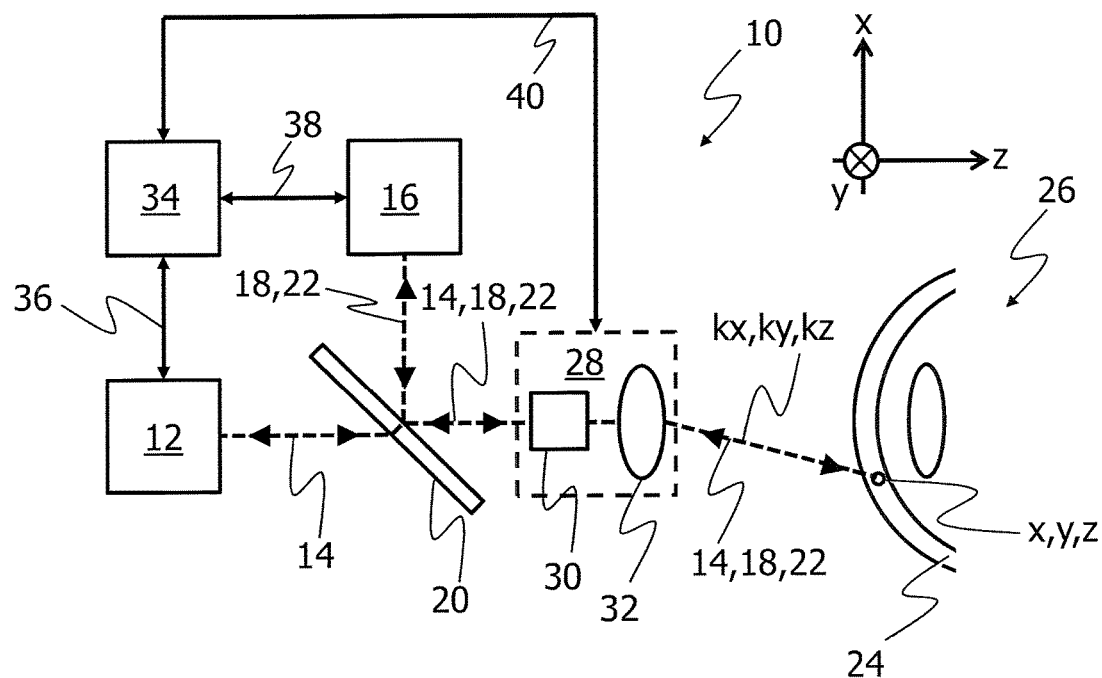

(51) Int. Cl.
*A61B 3/00* (2006.01)
*A61B 3/107* (2006.01)
*G01B 9/02* (2006.01)
*G01N 21/47* (2006.01)
*G02B 27/14* (2006.01)
*G01N 21/63* (2006.01)

(52) U.S. Cl.
CPC ..... *G01B 9/02029* (2013.01); *G01B 9/02091* (2013.01); *G01N 21/4795* (2013.01); *G02B 27/141* (2013.01); *G01N 2021/638* (2013.01)

(58) Field of Classification Search
USPC ............... 351/212, 200, 205–206, 209–211, 351/221–223, 245–246
See application file for complete search history.

(56) References Cited

U.S. PATENT DOCUMENTS

2008/0117427 A1* 5/2008 Teramura ........... G01N 21/4795 356/484
2009/0073453 A1* 3/2009 Hasegawa ............ A61B 5/0059 356/477
2012/0302862 A1* 11/2012 Yun ...................... A61B 5/0075 600/398

FOREIGN PATENT DOCUMENTS

| RU | 2290058 C2 | 12/2006 |
| WO | 2004/002298 A1 | 1/2004 |
| WO | 2007/034802 | 3/2007 |

OTHER PUBLICATIONS

G. Scarcelli et al.; "Brillouin Microscopy of Collagen Crosslinking: Noncontact Depth-Dependent Analysis of Corneal Elastic Modulus"; Investigative Ophthalmology & Visual Science; vol. 54; No. 2; Feb. 19, 2013; pp. 1418-1425; ISSN: 0146-0404.

Stephan Reiss et al.; "Spatially resolved Brillouin spectroscopy to determine the rheological properties of the eye lens"; Biomedical Optics Express; vol. 2; No. 8; Aug. 1, 2011; p. 2144; ISSN: 2156-7085.

* cited by examiner

DIAGNOSIS SYSTEM AND DIAGNOSIS METHOD

CROSS REFERENCE TO RELATED APPLICATIONS

This application is a section 371 national stage phase of International Application No. PCT/EP2013/071323, filed 11 Oct. 2013, titled "DIAGNOSIS SYSTEM AND DIAGNOSIS METHOD," which is hereby incorporated by reference in its entirety.

TECHNICAL FIELD

The present disclosure generally relates to a diagnosis system and a diagnosis method. More specifically, embodiments of the present disclosure relate to a diagnosis system for detection of keratoconus or other corneal degeneration impacting the biomechanical stability of the human cornea and a diagnosis method for detection of keratoconus or other corneal degeneration impacting the biomechanical stability of the human cornea. Still more specifically, embodiments of the present disclosure relate to a diagnosis system for early detection of keratoconus or other corneal degeneration impacting the biomechanical stability of the human cornea and a diagnosis method for early detection of keratoconus or other corneal degeneration impacting the biomechanical stability of the human cornea.

BACKGROUND

Keratoconus is a degenerative disorder of an eye, which is characterized by a non-inflammatory thinning and steepening of the central and/or para-central cornea. These structural changes cause the cornea to become of a more conical shape than its normal gradual curve and lead to non-reversible visual impairment of the patient's eye when untreated. Keratoconus caused structural changes of the cornea also aggravate or even preclude a LASIK (Laser Assisted in Situ Keratomileusis) surgery, since a LASIK treated cornea with a further progressed keratoconus may lead to a cornea ectasias later on.

A patient's visual impairment caused by keratoconus may be corrected by specially adapted eyeglasses or corneoscleral contact lenses. These corrections, however, do not work for a keratoconus in a late stage of its pathogenesis. In this case, only a so-called corneal crosslinking can be performed, which may stop or at least decelerate the pathogenesis. A complete visual rehabilitation, in turn, is not possible.

Therefore, it is desirable to detect keratoconus as early as possible.

Besides keratoconus, other corneal degeneration impacting the biomechanical stability of the human cornea exists. For example, pellucid marginal corneal degeneration (short: PMD; also known as keratotorus) is a degenerative corneal condition, which is typically characterized by a clear, bilateral thinning (ectasia) in the inferior and peripheral region of the cornea. In particular, the center of the cornea shows normal thickness with an intact central epithelium, but the inferior cornea exhibits a peripheral band of thinning. The portion of the cornea that is immediately adjacent to the limbus is spared, usually a strip of about a few millimeters. Further, Bowman's layer of the cornea may be absent, irregular or have ruptured areas.

In the following, the term keratoconus may represent any corneal degeneration impacting the biomechanical stability of the human cornea. Therefore, throughout this specification, the more specific term "keratoconus" may be replaced by the more general phrase "corneal degeneration impacting the biomechanical stability of the human cornea" or by any term representing corneal degeneration impacting the biomechanical stability of the human cornea, such as "pellucid marginal corneal degeneration".

Existing diagnosis systems and diagnosis methods for detecting keratoconus or other corneal degeneration impacting the biomechanical stability of the human cornea are merely based on a measuring of the topography of the cornea and a detection of a conical deformation in this topography. Therefore, the keratoconus or other corneal degeneration impacting the biomechanical stability of the human cornea can only be detected in a relatively late stage of the pathogenesis, in which the visual impairment of the patient is already advanced.

SUMMARY

In light of the above, there is a need to provide a diagnosis system and a diagnosis method, which allow an identification of a structural part of the cornea and an identification of a biomechanical property of this structural part of the cornea. More specifically, there is a need to provide a diagnosis system and a diagnosis method, which allow an early detection of keratoconus or other corneal degeneration impacting the biomechanical stability of the human cornea.

The present disclosure is based on the following findings:

To detect keratoconus or other corneal degeneration impacting the biomechanical stability of the human cornea in an early stage, it is desirable to acquire parameters of the cornea, by which an initiating keratoconus or other corneal degeneration impacting the biomechanical stability of the human cornea can be reliably diagnosed, before clinically manifested macroscopic structural changes of the cornea emerge.

The cornea or single parts of the inherent structure of the cornea may be considered as a linear-elastic, homogeneous and/or isotropic material. The inherent structure of the cornea comprises the corneal epithelium, Bowman's layer (also known as the anterior limiting membrane), the corneal stroma (also known as substantia propria), Dua's Layer, Descemet's membrane (also known as posterior limiting membrane) and the corneal endothelium.

For the etiology and during the pathogenesis of keratoconus or other corneal degeneration impacting the biomechanical stability of the human cornea, changes of biomechanical properties of the cornea are most likely to be relevant.

A bio-mechanical property may be represented by an elastomechanical property and/or a viscoelastic property. These are stiffness related properties. For example, a biomechanical property may be characterized by one or more of the following moduli:

The longitudinal modulus M (also known as the P-wave modulus or the constrained modulus), which can describe isotropic homogeneous materials. It may be defined as the ratio of axial stress to axial strain in a uniaxial strain state, where all the other non-axial strains are zero (i.e. zero lateral strain).

Young's modulus E (also referred to simply as the elastic modulus), which can describe tensile elasticity or the tendency of a medium to deform along an axis, when opposing forces are applied along that axis. It may be defined as the ratio of tensile stress to tensile strain.

The shear modulus G (also known as modulus of rigidity, μ, mu or Lamé's second parameter), which can describe an object's tendency to shear (the deformation of shape at constant volume), when acted upon by opposing forces. It may be defined as shear stress over shear strain. The shear modulus G may be part of the derivation of viscosity.

The bulk modulus K, which can describe volumetric elasticity or the tendency of a medium to deform in all directions, when uniformly loaded in all directions. It may be defined as volumetric stress over volumetric strain or as the inverse of compressibility κ (or kappa). The bulk modulus K may be understood as an extension of Young's modulus E to three dimensions.

Lamé's first parameter $\lambda_{Lame}$ (or lambda-Lamé), which can also describe tensile elasticity or the tendency of a medium to deform along an axis, when opposing forces are applied along that axis.

Poisson's ratio ν (or nu, also known as Poisson number), which can describe, when a medium is compressed in one direction, the tendency of the medium to expand in the other two directions perpendicular to the direction of compression. It may be defined as the negative ratio of transverse to axial strain or the fraction (or percent) of expansion divided by the fraction (or percent) of compression.

Stress may be defined as the restoring force caused due to the deformation divided by the area, to which the force is applied. Strain may be defined as the ratio of the change caused by the stress to the original state of the object.

For a homogeneous isotropic linear elastic medium, relations can be deduced that connect the above moduli among each other. For example, the bulk modulus K, Young's modulus E and the shear modulus G are interlinked via Poisson's ratio nu:

$$v = \frac{E}{2G} - 1 = \frac{3K-E}{6K} = \frac{3K-2G}{6K+2G}. \quad (1)$$

As a further example, bulk modulus K, shear modulus G and longitudinal modulus M are interlinked as follows:

$$M = K + \frac{4G}{3}. \quad (2)$$

Therefore, when some of the above moduli are known, other unknown moduli may be calculated therefrom.

To measure a bio-mechanical property, it may be employed a technique based on Brillouin scattering (short: BS). Brillouin scattering as such is known. In brief: A phonon (such as an acoustic mode, i.e. a sound wave) represents position dependent mass density variations inside a medium. Because of these local compressions, the optical density n (i.e. the index of refraction) of the medium locally changes. This leads to a spatially periodic optical density variation, which represents a diffraction grating for impinging coherent light. Brillouin scattering occurs, when coherent light interacts with such a spatially periodic optical density variation by being deflected or reflected there off. Since the phonon is traveling within the medium, the deflected/reflected light is subjected to a Doppler shift. That is, the Brillouin scattered photons change their energy, wherefore Brillouin scattering is an inelastic scattering process. The change in the photon energy corresponds to a change of the light's frequency f or the light's wavelength λ (wherein f and λ are interlinked by f·λ=c/n with c being the vacuum speed of light and n being the non-disturbed optical density of the medium) resulting in a frequency shift $f_B$ and a wavelength shift $\lambda_B$ up or down with respect to the frequency f and the wavelength λ of the un-deflected/un-reflected, i.e. impinging light. Consequently, the frequency of the inelastically Brillouin-scattered light is f±$f_B$ and the wavelength of the inelastically Brillouin-scattered light is λ±$\lambda_B$, respectively, and the spectrum of the Brillouin scattered light comprises beside elastically deflected/reflected light forming the so-called Rayleigh peak also inelastically Brillouin-scattered light forming at least one additional side peak or side band, the so-called Stokes and/or anti-Stokes peak or Stokes and/or anti-Stokes Brillouin peak. In general, the Brillouin scattered photons also change their propagation direction, wherein the frequency shift $f_B$ of the deflected/reflected BS light depends on the scattering angle θ between the impinging un-deflected/un-reflected light beam and the deflected/reflected Brillouin scattered light beam by:

$$f_B = \pm \frac{2 \cdot n \cdot V}{\lambda} \cdot \cos(\theta/2), \quad (3)$$

where:
n is the local optical density of the medium (when not changed by a phonon),
V is the velocity of the phonon (i.e. the speed of the sound wave or the acoustic velocity in the material; V=Λ·Ω with Λ being the wavelength of the phonon and Ω being the frequency of the phonon),
λ is the wavelength of the incidential (e.g., un-deflected/un-reflected) light wave in vacuum, and
θ is the scattering angle between the propagation direction of the impinging incidential (e.g., un-deflected/un-reflected) light wave and the propagation direction of the deflected/reflected Brillouin scattered light wave.

Per definition, the propagation direction of the impinging un-deflected/un-reflected light wave is anti-parallel to the propagation direction of the deflected/reflected Brillouin scattered light wave, when θ is zero (i.e. θ=0°). The "−" sign corresponds to the Stokes Brillouin peak and the "+" sign corresponds to the anti-Stokes Brillouin peak, respectively. A frequency shift $f_B$ corresponds to a wavelength shift $\lambda_B$ via $|f_B|\approx c \cdot n \cdot |\lambda_B|/\lambda^2$ for $|\lambda_B|<<\lambda$.

As the frequency shift $f_B$ depends on the scattering angle θ, each scattering angle θ relates to a specific frequency shift $f_B$. A maximum/minimum value of the frequency shift $f_B$=±2·n·V/λ is obtained for θ=0°, corresponding to a Brillouin scattered light beam, which is deflected/reflected into the opposite direction of the impinging un-scattered/un-deflected/un-reflected light wave. In the case of θ=0°, the frequency shift $f_B$ is also called longitudinal Brillouin shift.

By spectroscopically analyzing the Brillouin scattered light beam, bio-mechanical properties of the medium can be determined. For example, the complex valued longitudinal modulus M depends on the velocity of the phonon V by (Reiβ et al., "Spatially resolved Brillouin spectroscopy to determine the rheological properties of the eye lens", Biomedical Optics Express, Vol. 2, No. 8, p. 2144-2159):

$$M = M_1 + iM_2 = \rho \cdot V^2 + i \cdot \rho \cdot V^2 \cdot \frac{\Delta f_B}{f_B}, \quad (4)$$

where:
- ρ is the mass density of the medium, in which the phonon propagates, and
- $\Delta f_B$ is the line width of the Brillouin scattering caused side band of the BS deflected/reflected light beam.

The line width $\Delta f_B$ corresponds to the reciprocal of the lifetime of the phonon and characterizes the attenuation of the phonon (sound wave) during propagation through the medium. For example, the line width $\Delta f_B$ may be measured as the full width at half maximum (short: FWMH) of the Stokes or anti-Stokes Brillouin peak or any other suitable definition of a spectral width that characterizes a the frequency interval, over which the magnitude of all spectral components is equal to or greater than a specified fraction of the magnitude of the component having the maximum value.

When the Brillouin scattered light wave is deflected/reflected into the opposite direction of the impinging unscattered/un-deflected/un-reflected light wave (i.e.) θ=0°, the shear modulus G does not contribute (i.e. G=0) and the longitudinal modulus M equals the bulk modulus K (I.e. M=K), compare equation (2). In this case, equation (4) becomes:

$$M_1 = \frac{\lambda^2 \cdot \rho}{4 \cdot n^2} \cdot f_B^2, \text{ and} \quad (5)$$

$$M_2 = \frac{\lambda^2 \cdot \rho}{4 \cdot n^2} \cdot f_B \cdot \Delta f_B. \quad (6)$$

$M_1$ describes a elastomechanical property of the medium. $M_2$ describes a viscoelastic property of the medium.

From equations (5) and (6) it follows: By measuring the frequency shift $f_B$ of one of the side bands (Stokes or anti-Stokes) of a Brillouin scattered light beam backscattered from a medium, information can be obtained that relates to an elastomechanical property of the medium. By measuring the frequency shift $f_B$ of one of the side bands of a Brillouin scattered light beam backscattered from a medium and by measuring the line width $\Delta f_B$ of this side band, information can be obtained that relates to a viscoelastic property of the medium. More general, by providing data that represents the frequency shift $f_B$ and/or the line width $\Delta f_B$, information about bio-mechanical properties of the medium may be obtained.

In the present disclosure, a diagnosis system and a diagnosis method are provided.

The diagnosis system comprises an optical coherence tomography (short: OCT) device, which is configured to emit a first measuring light beam having a first wavelength $\lambda_1$. The diagnosis system additionally comprises a Brillouin scattering (short: BS) spectrometer, which is configured to emit a second light beam having a second wavelength $\lambda_2$, wherein the second wavelength $\lambda_2$ is different from the first wavelength $\lambda_1$. The diagnosis system also comprises a beam combiner, which is configured to combine the first light beam and the second light beam such that the first light beam and the second light beam propagate along a same optical path towards a cornea. The diagnosis system further comprises a beam guiding and focusing device, which is configured to focus the first light beam and the second light beam together at a predetermined position x,y,z on or in the cornea. By and from the cornea, the first and the second light beam may at least partially be deflected/reflected/scattered back into and along the opposite direction of the first and the second light beam that have entered the focus at the predetermined position x,y,z on/in the cornea before. The beam combiner splits the first and the second light beam backscattered from the cornea such that the first backscattered light beam enters the OCT device and the second backscattered light beam enters the BS spectrometer. The OCT device is configured to interferometrically analyze the first light beam backscattered from the cornea via the beam combiner to provide OCT data representing a position dependent structural property of the cornea. The BS spectrometer is configured to spectroscopically analyze the second light beam backscattered from the cornea via the beam combiner to provide BS data representing a position dependent frequency shift $f_B(x,y,z)$ of a Brillouin scattering caused side band of the backscattered second light beam.

By providing OCT data that represents a position dependent structural property of the cornea, spatially resolved information about the local structure of the cornea may be obtained. Additionally, by providing BS data that represents the position dependent frequency shift $f_B(x,y,z)$ of the Brillouin scattering caused side band of the backscattered second light beam, spatially resolved information about an elastomechanical and thus a bio-mechanical property of the cornea may be obtained. As the first and the second light beam are focused together to the same local position x,y,z on or in the cornea, the local structure and the bio-mechanical property relate to one and the same position x,y,z on/in the cornea. Hence, the diagnosis system allows an identification of a structural part of the cornea and an identification of a biomechanical property of this structural part of the cornea.

Further, when using the diagnosis system for monitoring the cornea over a specific time period, both changes of the structure of the cornea and changes of the biomechanical property of the cornea can be observed in a spatially resolved and locally correlated manner. Such changes may indicate either the integrity of the cornea or an initiating or even advanced keratoconus of the cornea. Consequently, the diagnosis system allows an early detection of keratoconus or other corneal degeneration impacting the biomechanical stability of the human cornea.

Further advantages of the diagnosis system are the following: The structural and bio-mechanical characterization of the cornea can be performed fast and contactless, for example, non-invasive and in-vivo, since it is only based on the emission of the first and the second light beam. Furthermore, because of the beam combiner combining the first and the second light beam, the diagnosis system allows a simultaneous measurement of the structural and biomechanical properties of the cornea. This not only reduces the overall diagnosis time, but also ensures a temporal correlation of the structural and biomechanical properties of the cornea.

The OCT device may be based on OCT in the Fourier domain (in short: FD-OCT), on OCT in the spectral domain (short: SD-OCT) or on OCT employing in a swept-source (short: SS-OCT). FD-OCT and SD-OCT typically uses a light source that continuously emits broadband light of a particular spectral bandwidth $\Delta\lambda_1$. SS-OCT typically uses a light source that is spectrally tunable (i.e. with respect to the wavelength $\lambda_1$ of the emitted light), which instantaneously emits spectrally narrow-band light and which is tuned continuously across a spectral bandwidth $\Delta\lambda_1$. The first wavelength $\lambda_1$ of the first light beam may be the central wavelength of the OCT-spectrum, i.e. of the spectral bandwidth $\Delta\lambda_1$. The OCT device may have an axial resolution of 10 μm or smaller. The OCT device may have a lateral resolution of 100 μm or smaller. The first light beam may be a first coherent light beam. The first wavelength $\lambda_1$ of the first light beam may be around 800 nm. The spectral bandwidth $\Delta\lambda_1$ of the OCT device may be around 100 nm.

The OCT device may be configured to interferometrically analyze the first light beam backscattered from the cornea via the beam combiner to provide OCT data representing an image of the cornea at or in the vicinity of the focal position x,y,z. The OCT device may be configured to interferometrically analyze the first light beam backscattered from the cornea via the beam combiner to provide OCT data representing a position dependent optical density n(x,y,z) of the cornea (for example, when n(x,y,z) is not disturbed by a phonon), a position dependent mass density ρ(x,y,z) of the cornea and/or a position dependent reflectivity r(x,y,z) of the cornea.

Scattering is a general physical process, where some form of radiation, such as light, is forced to deviate from a straight trajectory by one or more localized non-uniformities in the medium, through which it passes. This may also include deviation of reflected radiation, for example, from the angle predicted by the law of reflection. In turn, reflection or deflection may represent scattering. In particular, any light beam, which is backscattered, may also be considered to be reflected and/or deflected, and vice versa. In this sense, throughout this specification, the term "backscattered" may be replaced by "reflected" and/or by "defleced" or by any arbitray combination thereof.

The BS spectrometer may have a resolution of 100 μm or smaller. The second light beam may be a second coherent light beam. The second wavelength $\lambda_2$ of the (i.e. un-deflected, un-reflected, un-scattered) second light beam may be around 532 nm. The line width, for example, the FWHM of the spectral distribution, of the second light beam may be equal to or smaller than 10 MHz.

The BS spectrometer may be configured to spectroscopically analyze the second light beam backscattered from the cornea via the beam combiner to provide BS data representing also a position dependent line width $\Delta f_B(x,y,z)$ of the Brillouin scattering caused side band of the backscattered second light beam. This information represents a viscoelastic property of the cornea. Thus, the diagnosis system may allow an identification of a structural part of the cornea and an identification of not only an elastomechanical, but also an viscoelastic property of this structural part of the cornea.

The beam guiding and focusing device may be configured to adjust the directional orientation $k_x,k_y,k_z$ of the first light beam and the second light beam, along which the first light beam and the second light beam enter the focus on or in the cornea. The BS spectrometer may be further configured to spectroscopically analyze the second light beam backscattered from the cornea via the beam combiner to provide BS data also representing a direction dependent frequency shift $f_B(x,y,z,k_x,k_y,k_z)$ of the Brillouin scattering caused side band. In other words: The BS spectrometer may not only provide BS data representing a frequency shift $f_B(x,y,z,k_x,k_y,k_z)$ of the Brillouin scattering caused side band depending on the position of the focus of the second light beam, but also depending on the direction, along which the second light beam enters the focus. This allows a measuring of an elastomechanical property of the cornea in terms of a tensor representation. For example, the position and direction resolved measuring of the frequency shift $f_B(x,y,z,k_x,k_y,k_z)$ may be used to calculate a tensor-modulus such as $(M_1)_j^i$. As a consequence, an anisotropic elastomechanical property of the cornea can be observed, which may give further indication for an initiating keratoconus or other corneal degeneration impacting the biomechanical stability of the human cornea of the cornea.

The beam guiding and focusing device may be configured to adjust the directional orientation $k_x,k_y,k_z$ of the first light beam and the second light beam, along which the first light beam and the second light beam enter the focus on or in the cornea. The BS spectrometer may be further configured to spectroscopically analyze the second light beam backscattered from the cornea via the beam combiner to provide BS data also representing a direction dependent line width $\Delta f_B(x,y,z,k_x,k_y,k_z)$ of the Brillouin scattering caused side band. In other words: The BS spectrometer may not only provide BS data representing a line width $\Delta f_B(x,y,z,k_x,k_y,k_z)$ of the Brillouin scattering caused side band depending on the position of the focus of the second light beam, but also depending on the direction, along which the second light beam enters the focus. This allows a measuring of a viscoelastic property of the cornea in terms of a tensor representation. For example, the position and direction resolved measuring of the frequency shift $f_B(x,y,z,k_x,k_y,k_z)$ and the line width $\Delta f_B(x,y,z,k_x,k_y,k_z)$ may be used to calculate a tensor-modulus such as $(M_2)_j^i$. As a consequence, an anisotropic viscoelastic property of the cornea can be observed, which may give further indication for an initiating keratoconus or other corneal degeneration impacting the biomechanical stability of the human cornea of the cornea.

The diagnosis system may comprise a control and analysis device. The control and analysis device may be configured to control the beam guiding and focusing device to scan the predetermined position x,y,z of the focus on or in the cornea in a one-, two or- three-dimensional manner and/or to scan the directional orientation $k_x,k_y,k_z$ of the first light beam and the second light beam along that the first light beam and the second light beam enter the focus on or in the cornea.

The control and analysis device may be configured to calculate a spatially resolved topological and/or morphological structure from the OCT data. The control and analysis device may be configured to generate from the OCT data an image of the cornea at or in the vicinity of the focal position x,y,z. Hence, for example, a topography or morphology of the cornea may be acquired. Such an acquisition may comprise the front and/or back side of cornea or the inherent structure of the cornea such as the corneal epithelium, Bowman's layer (also known as the anterior limiting membrane), the corneal stroma (also known as substantia propria), Dua's Layer, Descemet's membrane (also known as posterior limiting membrane) and the corneal endothelium.

The control and analysis device may be configured to generate from the OCT data at the focal position x,y,z a local optical density n(x,y,z) of the cornea (for example, when n(x,y,z) is not disturbed by a phonon), a local mass density p(x,y,z) of the cornea and/or a local reflectivity r(x,y,z) of the cornea. For example, the control and analysis device may be configured to identify by image processing from the OCT data, in which part of the inherent structure of the cornea the focal position x,y,z is localized, and to associate for this inherent structural part a corresponding local optical density n(x,y,z) of the cornea, a corresponding local mass density p(x,y,z) of the cornea and/or a corresponding local reflectivity r(x,y,z) by use of a look-up table previously stored in a memory of the control and analysis device. Hence, for each point x,y,z within a topography/morphology of the cornea, the corresponding local optical density n(x,y,z), local mass density p(x,y,z) and/or local reflectivity r(x,y,z) of the cornea can be determined. The control and analysis device may be configured to calculate spatially and/or directionally resolved elastomechanical and/or viscoelastic properties of the cornea from the BS data. This allows 1D, 2D or 3D OCT imaging combined with spatially and/or directionally correlated 1D, 2D or 3D BS spectroscopy. Hence, for each point x,y,z within a topography/morphology of the cornea, the corresponding local elastomechanical and/or viscoelastic properties may be determined, thus associating the topography/morphology of the cornea with the rheology of the cornea. As a consequence, a full faced testing of the integrity of the cornea can be performed, thereby determining biomechanical properties (such as the stiffness) of the cornea taking account of the individual structure/form of the cornea. For example: Where there is anomaly or deviation in the morphology of the examined cornea in comparison to a healthy or normal cornea (such as a locally thinned out epithelium), precise measurements of the elastomechanical and/or viscoelastic parameters can be performed in order to monitor any change in the biomechanical properties.

The control and analysis device may be configured to calculate $$M_1 = \frac{\lambda_2^2 \cdot \rho}{4 \cdot n^2} \cdot f_B^2 \text{ and/or}$$

$$M_2 = \frac{\lambda_2^2 \cdot \rho}{4 \cdot n^2} \cdot f_B \cdot \Delta f_B,$$

where:
$M_1$ is the real part of the complex longitudinal modulus $M=M_1+iM_2$ of the cornea,
$M_2$ is the imaginary part of the complex longitudinal modulus $M=M_1+iM_2$ of the cornea,
$\lambda_2$ is the second wavelength of the second light beam,
$\rho$ is the mass density of the cornea,
n is the optical density of the cornea,
$f_B$ is the frequency shift of the Brillouin scattering caused side band of the backscattered second light beam, and
$\Delta f_B$ is the line width of the Brillouin scattering caused side band of the backscattered second light beam.

For the calculation of $M_1$ and/or $M_2$, the control and analysis device may be configured to read out a constant mass density $\rho=\rho(x,y,z)=\rho_{constant}$ for the local mass density $\rho(x,y,z)$ and/or to read out a constant local optical density $n=n(x,y,z)=n_{constant}$ for the local optical density $n(x,y,z)$ from a memory of the control and analysis device. For the calculation of $M_1$ and/or $M_2$, the control and analysis device may be configured to generate from the OCT data at the focal position x,y,z a local optical density $n(x,y,z)$ of the cornea (for example, when $n(x,y,z)$ is not disturbed by a phonon), a local mass density $\rho(x,y,z)$ of the cornea.

The analysis device may be configured to spatially correlate the OCT data with the BS data such that for each spatial position the topological and/or morphological structure of the cornea is associated with the corresponding elastomechanical and/or viscoelastic properties of the cornea. As a result, of the same area of the cornea it is known both the morphology (such as highly resolved local curving, thickness variations of the stroma, thickness of the epithelium dislocation of Bowman's membrane and the like) and correlated therewith spatially and/or directionally resolved elastomechanical and/or viscoelastic parameters. Therefore, spatially resolved geometry of the cornea can be extracted together with spatially and directionally resolved stiffness of the cornea.

The beam combiner may be a dichroic mirror or a dispersive optical element such as an optical diffraction grating or a prism or the like. The beam combiner may have a first reflectivity at least within a first wavelength range $R_1$ covering at least the first wavelength $\lambda_1$ of the first light beam and the spectral bandwidth $\Delta\lambda_1$ of the OCT device. The minimum value of the first wavelength range $R_1$ may be equal or smaller than $\lambda_1-\Delta\lambda_1/2$. The maximum value of the first wavelength range $R_1$ may be equal or larger than $\lambda_1+\Delta\lambda_1/2$. The beam combiner may have a second reflectivity at least within a second wavelength range $R_2$ covering the second wavelength $\lambda_2$ of the second light beam and a spectral bandwidth $\Delta\lambda_2$. The minimum value of the second wavelength range $R_2$ may be equal or smaller than $\lambda_2-\Delta\lambda_2/2$. The maximum value of the second wavelength range $R_2$ may be equal or larger than $\lambda_2+\Delta\lambda_2/2$.

The beam combiner may be configured such that the first wavelength range $R_1$ and the second wavelength range $R_2$ are disjoint. The beam combiner may be configured such that the first reflectivity and the second reflectivity are different. For example, the first reflectivity of the beam combiner may be around 10% or less, e.g., 5% or less, and the second reflectivity of the beam combiner may be around 90% or more, e.g., 95% or more, or vice versa. The second spectral bandwidth $\Delta\lambda_2$ may correspond to around 10, 15, 20, 25, 30, 50 or 100 GHz.

The term reflectivity may represent the reflectance or the fraction of incident electromagnetic power reflected. A reflectivity of less than 50% may represent or be understood as a transmittance or a transmission. In particular, a value $T(\lambda)$ of transmittance or transmission of the beam combiner may be given by 100% minus a value $R(\lambda)$ of the reflectivity of the beam combiner, i.e. $T(\lambda)=1-R(\lambda)$. In other words: The beam combiner may be configured such that the absorption of light within the beam combiner is small, negligible or even zero. For example, a first reflectivity of the beam combiner around 10% or less, e.g., 5% or less, may represent or be understood as a transmittance or a transmission of the beam combiner around 90% or more, e.g., 95% or more.

It is pointed out the phrase "vice versa" in "the first reflectivity of the beam combiner may be around 10% or less, e.g. 5% or less, and the second reflectivity of the beam combiner may be around 90% or more, e.g. 95% or more, or vice versa". This means that the beam combiner may be configured to combine the first light beam and the second light beam by transmitting the first light beam and reflecting the second light beam. As an alternative, the beam combiner may be configured to combine the first light beam and the second light beam by reflecting the first light beam and by transmitting the second light beam. These alternatives allow a rearrangement or an interchange of the OCT device and the BS spectrometer.

A diagnosis method comprises the steps of:
emitting an optical coherence tomography (short: OCT) light beam having a first wavelength $\lambda_1$ from an OCT device,
emitting a second light beam having a second wavelength $\lambda_2$ different from the first wavelength $\lambda_1$ from a Brillouin scattering (short: BS) spectrometer,
combining the first light beam and the second light beam by a beam combiner such that the first light beam and the second light beam propagate along a same optical path towards a cornea,
focusing the first light beam and the second light beam together at a predetermined position x,y,z on or in the cornea by a beam guiding and focusing device,
interferometrically analyzing the first light beam backscattered from the cornea via the beam combiner by the OCT device to provide OCT data representing a position dependent structural property of the cornea, and
spectroscopically analyzing the second light beam backscattered from the cornea via the beam combiner by the BS spectrometer to provide BS data representing a position dependent frequency shift $f_B(x,y,z)$ of a Brillouin scattering caused side band of the backscattered second light beam.

To the extent that a diagnosis method or individual steps of a diagnosis method is/are described in this description, the diagnosis method or individual steps of the diagnosis method can be executed by an appropriately configured diagnosis system and/or an individual device of the diagnosis system. Analogous remarks apply to the elucidation of the operation mode of a diagnosis system and/or individual devices of the diagnosis system that execute(s) diagnosis method steps. To this extent, apparatus features and method features of this description are equivalent.

Figure 2:
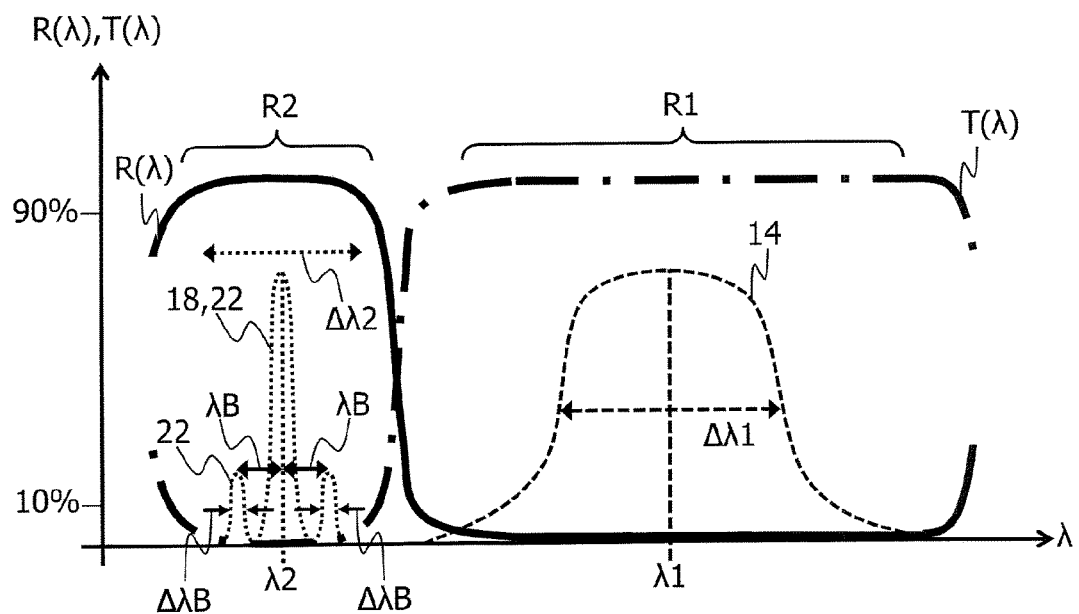
Figure 3:
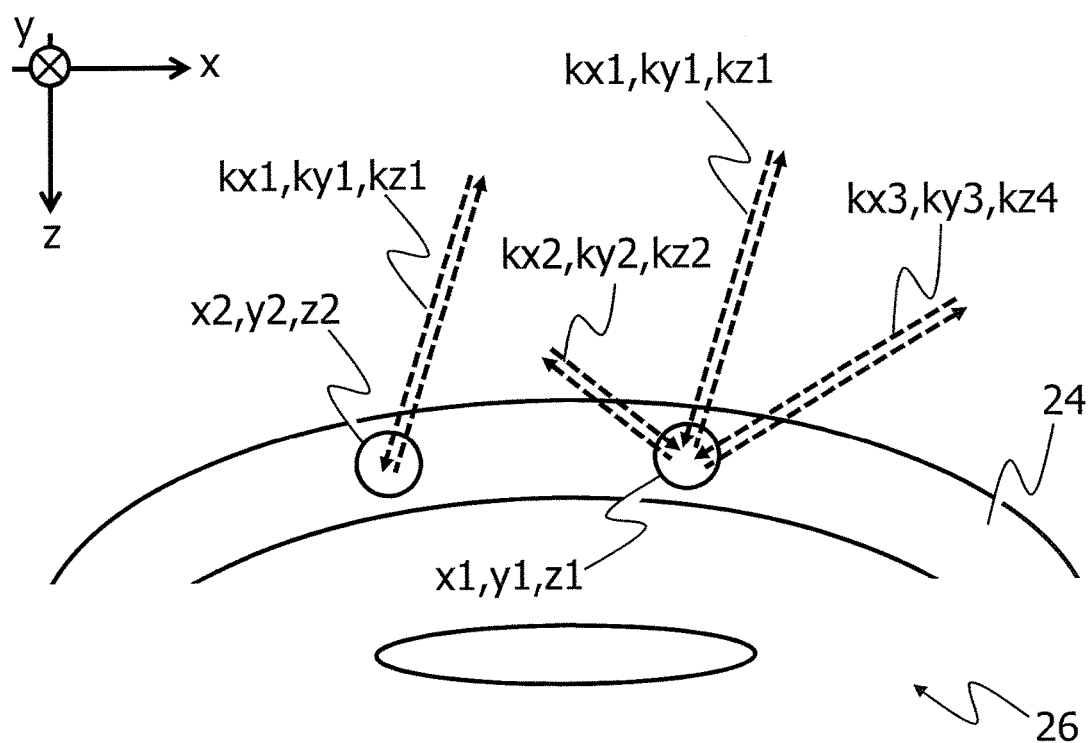

Further features, advantages and technical effects of the disclosure will become apparent from the following description of exemplary embodiments with reference to the accompanying drawings, in which:

FIG. 1 schematically illustrates a diagnosis system,

FIG. 2 schematically illustrates the transmission and reflectivity of a beam combiner of the diagnosis system in FIG. 1 (not drawn to scale), and FIG. 3 schematically illustrates a diagnosis method executed by the diagnosis system of FIG. 1.

FIG. 1 shows a diagnosis system 10, which comprises an optical coherence tomography (short: OCT) device 12, which is configured to emit a first coherent light beam 14 having a first wavelength $\lambda_1$ around 800 nm. As an example, the OCT device 12 is based on OCT in the Fourier domain (in short: FD-OCT) and comprises a light source that emits the first light beam 14 as broadband light of a particular spectral bandwidth $\Delta\lambda_1$, i.e. the full width at half maximum (short: FWHM) of the spectral distribution of the first light beam 14 is around 100 nm. The first wavelength $\lambda_1$ of the first light beam 14 is the central wavelength of the OCT-spectrum, i.e. of the spectral bandwidth $\Delta\lambda_1$. The spectral distribution of the first light beam 14 is schematically illustrated by the dashed lines in FIG. 2. The OCT device has exemplarily an axial resolution of less than 10 μm.

The diagnosis system 10 additionally comprises a Brillouin scattering (short: BS) spectrometer 16, which is configured to emit a second coherent light beam 18 having a second wavelength $\lambda_2$ around 532 nm. The FWHM of the spectral distribution of the (un-scattered) second light beam 18 is less than 10 MHz. The spectral distribution of the (un-scattered) first light beam 18 is schematically illustrated by the dot lined peak at $\lambda_2$ in FIG. 2.

A beam combiner 20 of the diagnosis system 10 is configured to combine the first light beam 14 and the second light beam 18 such that the first light beam 14 and the second light beam 18 propagate along a same optical path 22 towards a cornea 24 of an eye 26.

As an example, the beam combiner 20 is realized as a dichroic mirror. As shown in FIG. 2, the beam combiner 20 has a transmission $T(\lambda)$ around 90% or less e.g., around 95% or more at least within a first wavelength range $R_1$ covering at least the first wavelength $\lambda_1$ of the first light beam 14 and the spectral bandwidth $\Delta\lambda_1$ of the OCT device 12. The minimum value of the first wavelength range $R_1$ is smaller than $\lambda_1-\Delta\lambda_1/2$ and the maximum value of the first wavelength range $R_1$ is larger than $\lambda_1+\Delta\lambda_1/2$. The beam combiner 20 has a reflectivity $R(\lambda)$ around 90% or more, e.g., 95% or more at least within a second wavelength range $R_2$ covering the second wavelength $\lambda_2$ of the second light beam 18 and a spectral bandwidth $\Delta\lambda_2$. It applies: $T(\lambda)=1-R(\lambda)$. The second spectral bandwidth $\Delta\lambda_2$ corresponds to around 30 GHz. The minimum value of the second wavelength range $R_2$ is smaller than $\lambda_2-\Delta\lambda_2/2$ and the maximum value of the second wavelength range $R_2$ is larger than $\lambda_2+\Delta\lambda_2/2$. The beam combiner 20 is configured such that the first wavelength range $R_1$ and the second wavelength range $R_2$ are disjoint.

The diagnosis system 10 further comprises a beam guiding and focusing device 28, which is arranged in the optical path 22 between the beam combiner 20 and the cornea 24. The beam guiding and focusing device 28 is configured to focus the first light beam 14 and the second light beam 18 together at a predetermined position x,y,z on or in the cornea 24. In this sense, the beam guiding and focusing device 28 is configured to adjust the spatial position x,y,z, where the first light beam 14 and the second light beam 18 are focused in or on the cornea 24. Additionally, the beam guiding and focusing device 28 is configured to adjust the directional orientation $k_x, k_y, k_z$ of the first light beam 14 and the second light beam 18, along which the first light beam 14 and the second light beam 18 enter the focus on or in the cornea 24 at the spatial position x,y,z, (compare FIGS. 1 and 3).

For example, beam guiding and focusing device 28 comprises a scanning unit 30 with at least one pair of galvanometer mirrors (not shown) rotatable around two perpendicularly oriented rotation axis. The scanning unit 30 is configured to scan the focal position x,y,z in a two-dimensional manner along spatial directions x and y (compare the coordinate system in FIGS. 1 and 3). The beam guiding and focusing device 28 further comprises an objective 32 for focusing the first light beam 14 and the second light beam 18 on or in the cornea 24 and for collecting light, which has been deflected/reflected/scattered by and from the cornea 24. The objective 32 is configured such that a lateral resolution of the OCT device 12 and the resolution of the BS spectrometer 16 is less than 100 μm, e.g., 50 μm. The focal length of the objective 32 is changeable along spatial direction z to scan the focal position x,y,z in a one-dimensional manner along spatial direction z (compare again the coordinate system in FIGS. 1 and 3).

By and from the cornea 24, the first and the second light beam 14, 18 are partially deflected/reflected/scattered back into and along the opposite direction of the first and the second light beam 14, 18 that have entered the focus at the predetermined position x,y,z on/in the cornea 24 before (compare the arrows along 14, 18, 22 in FIG. 1). The backscattered first and second light beams 14, 18 re-pass through the beam guiding and focusing device 28 towards the beam combiner 20. The beam combiner 20 splits the first and the second light beam 14, 18 backscattered from the cornea 24 such that the first backscattered light beam 14 enters the OCT device 12 and the second backscattered light beam 18 enters the BS spectrometer 16. In this sense, the beam combiner 20 is also a beam splitter.

The OCT device 12 is configured to interferometrically analyze the first light beam 14 backscattered from the cornea 24 via the beam combiner 20 to provide OCT data representing a position dependent structural property of the cornea 24. For example, the OCT device 12 is configured to provide OCT data representing an image of the cornea 24 at or in the vicinity of the focal position x,y,z and to provide OCT data representing a position dependent optical density $n(x,y,z)$ of the cornea 24 as well as a position dependent mass density $\rho(x,y,z)$ of the cornea 24.

The BS spectrometer 16 is configured to spectroscopically analyze the second light beam 18 backscattered from the cornea 24 via the beam combiner 20 to provide BS data representing a position and direction dependent frequency shift $f_B(x,y,z)$ as well as a position and direction dependent line width $\Delta f_B(x,y,z)$ of the Brillouin scattering caused side band of the backscattered second light beam 18. The spectral distribution of the Brillouin scattered second light beam 18 is schematically illustrated by the dot lined peak at $\lambda_2$ and the two dot lined side bands/peaks in FIG. 2. The frequency shift $f_B$ corresponds to a wavelength shift $\lambda_B$ via $|f_B| \approx c \cdot n \cdot |\lambda_B|/\lambda^2$ and frequency line width $\Delta f_B$ corresponds to a wavelength line width $\Delta \lambda_B$ via $|\Delta f_B| \approx c \cdot n \cdot |\Delta \lambda_B|/\lambda^2$ for $|\lambda_B| \ll \lambda$.

The diagnosis system 10 also comprises a control and analysis device 34. The control and analysis device 34 is connected with the OCT device 12 and the BS spectrometer 16 via respective connection lines 36 and 38 to control the OCT device 12 and the BS spectrometer 16 and to receive the OCT data and the BS data. The control and analysis device 34 is also connected to the beam guiding and focusing device 28 via connecting line 40 to control the beam guiding and focusing device 28 such that the beam guiding and focusing device 28 scans the predetermined position x,y,z of the focus on or in the cornea 24 in a predetermined three-dimensional manner and also scans the directional orientation $k_x, k_y, k_z$ along that the first light beam 14 and the second light beam 18 enter the focus on or in the cornea 24 at x,y,z in a predetermined manner.

For example, both the first and the second beam 14, 18 are indicated as dashed arrows in FIG. 3. In a first state of the beam guiding and focusing device 28, the first and the second beam 14, 18 enter a first focal position x1,y1,z1 along a first direction kx1,ky1,kz1 and are scattered therefrom back into the opposite direction of kx1,ky1,kz1. In a second state of the beam guiding and focusing device 28, the first and the second beam 14, 18 enter the first focal position x1,y1,z1 along a second direction kx2,ky2,kz2 and are scattered therefrom back into the opposite direction of kx2,ky2,kz2. In a third state of the beam guiding and focusing device 28, the first and the second beam 14, 18 enter the first focal position x1,y1,z1 along a third direction kx3,ky3,kz3 and are scattered therefrom back into the opposite direction of kx3,ky3,kz3. In a fourth state of the beam guiding and focusing device 28, the first and the second beam 14, 18 enter a second focal position x2,y2,z2 along the first direction kx1,ky1,kz1 and are scattered therefrom back into the opposite direction of kx1,ky1,kz1. The first direction kx1,ky1,kz1 may correspond to the x direction, the second direction kx2,ky2,kz2 may correspond to the y direction and the third direction kx3,ky3,kz3 may correspond to the z direction of the coordinate system of the coordinate system as shown in FIGS. 1 and 3.

The control and analysis device 34 is configured to calculate a spatially resolved topological and morphological structure from the OCT data. For example, the control and analysis device 34 is configured to generate from the OCT data an image of the cornea 24 at or in the vicinity of the focal position x,y,z. Additionally, the control and analysis device 34 is configured to generate from the OCT data at the focal position x,y,z a local optical density n(x,y,z) (when n(x,y,z) is not disturbed by a phonon) and a local mass density p(x,y,z) of the cornea 24. For example, the control and analysis device 34 identifies by image processing from the OCT data, in which part of the inherent structure of the cornea 24 the focal position x,y,z is localized, and associates for this inherent structural part a corresponding local optical density n(x,y,z) as well as a corresponding local mass density p(x,y,z) of the cornea 24 by use of a look-up table stored in a memory (not shown) of the control and analysis device 34. Hence, for each point x,y,z within a topography/morphology of the cornea, the corresponding local optical density n(x,y,z) and local mass density p(x,y,z) of the cornea 24 is determined.

The control and analysis device 34 is also configured to calculate spatially and directionally resolved elastomechanical and viscoelastic properties of the cornea 24 from the BS data. For example, the control and analysis device 34 calculates $$M_1 = \frac{\lambda_2^2 \cdot \rho}{4 \cdot n^2} \cdot f_B^2 \text{ and}$$

$$M_2 = \frac{\lambda_2^2 \cdot \rho}{4 \cdot n^2} \cdot f_B \cdot \Delta f_B,$$

where:
$M_1$ is the real part of the complex longitudinal modulus $M = M_1 + iM_2$ of the cornea 24,
$M_2$ is the imaginary part of the complex longitudinal modulus $M = M_1 + iM_2$ of the cornea 24,
$\lambda_2$ is the second wavelength of the second light beam 18,
$\eta = \eta(x,y,z)$ is the local mass density of the cornea 24 extracted from the OCT data,
n=n(x,y,z) is the local optical density of the cornea 24 also extracted from the OCT data,
$f_B$ is the frequency shift of the Brillouin scattering caused side band of the backscattered second light beam 18 extracted from the BS data, and
$\Delta f_B$ is the line width of the Brillouin scattering caused side band of the backscattered second light beam 18 extracted from the BS data.

The control and analysis device 34 is further configured to spatially correlate the OCT data with the BS data such that for each spatial position x,y,z the topological and morphological structure of the cornea 24 is associated with the corresponding elastomechanical and viscoelastic properties of the cornea 24.

As a result, for the same area of the cornea 24 it is known both the morphology (such as highly resolved local curving, thickness variations of the stroma, thickness of the epithelium dislocation of Bowman's membrane and the like) and correlated therewith spatially and directionally resolved elastomechanical and viscoelastic parameters. Therefore, it can be extracted spatially resolved geometry of the cornea 24 together with spatially and directionally resolved stiffness of the cornea 24.

Unless expressly stated otherwise, identical reference symbols in the Figures stand for identical or identically-acting elements. Also, an arbitrary combination of the features and/or modifications elucidated in the Figures in connection with individual embodiments is conceivable.

The invention claimed is:
1. A diagnosis system, comprising:
an optical coherence tomography (OCT) device configured to emit a first light beam having a first wavelength $\lambda_1$;
a Brillouin scattering (BS) spectrometer configured to emit a second light beam having a second wavelength $\lambda_2$ different from the first wavelength $\lambda_1$;
a beam combiner comprising a dichroic mirror arranged:
in the optical path of the first light beam and having a first reflectivity for transmitting the first light beam in an optical path towards a cornea, the first reflectivity being at least within a first wavelength range

$R_1$ covering at least the first wavelength $\lambda_1$ of the first light beam and a spectral bandwidth $\Delta\lambda_1$ of the OCT device; and in the optical path of the second light beam and having a second reflectivity for reflecting the second light beam in the optical path towards the cornea, the second reflectivity at least within a second wavelength range $R_2$ covering the second wavelength $\lambda_2$ of the second light beam and a spectral bandwidth $\Delta\lambda_2$, wherein the first wavelength range $R_1$ and the second wavelength range $R_2$ are disjoint and the first reflectivity and the second reflectivity are different;

wherein the transmission of the first light beam and the reflection of the second light beam combines the first light beam and the second light beam and propagates the combined beam along the same optical path towards a cornea;

a beam guiding and focusing device configured to focus the first light beam and the second light beam together at a predetermined position (x,y,z) on or in the cornea; and a control and analysis device configured to scan a directional orientation ($k_x,k_y,k_z$) of the first light beam and the second light beam along that the first light beam and the second light beam enter the focus (x,y,z) on or in the cornea;

the OCT device is further configured to interferometrically analyze the first light beam backscattered from the cornea via the beam combiner to provide OCT data representing a position dependent structural property of the cornea; and the BS spectrometer is further configured to spectroscopically analyze the second light beam backscattered from the cornea via the beam combiner to provide BS data representing a position dependent frequency shift ($f_B$(x,y,z)) of a Brillouin scattering caused side band of the backscattered second light beam;

wherein the control and analysis device further configured to:
control the beam guiding and focusing device to scan the predetermined position (x,y,z) in a three-dimensional manner;
calculate, using a lookup table in a memory location, a local optical density and a local mass density of the cornea.

2. The diagnosis system of claim 1, wherein the BS spectrometer is further configured to spectroscopically analyze the second light beam backscattered from the cornea via the beam combiner to provide BS data representing also a position dependent line width ($\Delta f_B$(x,y,z)) of the Brillouin scattering caused side band of the backscattered second light beam.

3. The diagnosis system of claim 1, wherein:
the beam guiding and focusing device is further configured to adjust the directional orientation ($k_x,k_y,k_z$) of the first light beam and the second light beam, along which the first light beam and the second light beam enter the focus on or in the cornea; and the BS spectrometer is further configured to spectroscopically analyze the second light beam backscattered from the cornea via the beam combiner to provide BS data also representing a direction dependent frequency shift ($f_B$(x,y,z,$k_x,k_y,k_z$)) of the Brillouin scattering caused side band.

4. The diagnosis system of claim 1, wherein:
the beam guiding and focusing device is further configured to adjust the directional orientation ($k_x,k_y,k_z$) of the first light beam and the second light beam, along which the first light beam and the second light beam enter the focus on or in the cornea; and the BS spectrometer is further configured to spectroscopically analyze the second light beam backscattered from the cornea via the beam combiner to provide BS data also representing a direction dependent line width ($\Delta f_B$(x,y,z,$k_x,k_y,k_z$)) of the Brillouin scattering caused side band.

5. The diagnosis system of claim 1, the control and analysis device further configured to:
control the beam guiding and focusing device to scan the predetermined position (x,y,z) of the focus on or in the cornea in a one-, two-, or three-dimensional manner; and calculate a spatially resolved topological or morphological structure from the OCT data or calculate spatially resolved elastomechanical or viscoelastic properties of the cornea from the BS data.

6. The diagnosis system of claim 5, wherein the control and analysis device is further configured to calculate $$M_1 = \frac{\lambda_2^2 \cdot \rho}{4 \cdot n^2} \cdot f_B^2 \text{ or}$$

$$M_2 = \frac{\lambda_2^2 \cdot \rho}{4 \cdot n^2} \cdot f_B \cdot \Delta f_B,$$

where $M_1$ is the real part of the complex longitudinal modulus $M=M_1+iM_2$ of the cornea, $M_2$ is the imaginary part of the complex longitudinal modulus $M=M_1+iM_2$ of the cornea, $\lambda_2$ is the second wavelength of the second light beam, $\rho$ is the mass density of the cornea, n is the optical density of the cornea, $f_B$ is the frequency shift of the Brillouin scattering caused side band of the backscattered second light beam, and $\Delta f_B$ is the line width of the Brillouin scattering caused side band of the backscattered second light beam.

7. The diagnosis system of claim 5, wherein the control and analysis device is further configured to spatially correlate the OCT data with the BS data such that for each spatial position (x,y,z) the topological or morphological structure of the cornea is associated with the corresponding elastomechanical or viscoelastic properties of the cornea.

* * * * *